(12) United States Patent
Fruchey et al.

(10) Patent No.: US 8,895,779 B2
(45) Date of Patent: *Nov. 25, 2014

(54) PROCESSES FOR PRODUCING MONOAMMONIUM ADIPATE AND CONVERSION OF MONOAMMONIUM ADIPATE TO ADIPIC ACID

(75) Inventors: Olan S. Fruchey, Hurricane, WV (US); Leo E. Manzer, Wilmington, DE (US); Dilum Dunuwila, Princeton, NJ (US); Brian T. Keen, Pinch, WV (US); Brooke A. Albin, Charleston, WV (US); Nye A. Clinton, Hurricane, WV (US); Bernard D. Dombek, Charleston, WV (US)

(73) Assignee: BioAmber Inc., Plymouth, MN (US)

( * ) Notice: Subject to any disclaimer, the term of this patent is extended or adjusted under 35 U.S.C. 154(b) by 475 days.

This patent is subject to a terminal disclaimer.

(21) Appl. No.: 13/086,801

(22) Filed: Apr. 14, 2011

(65) Prior Publication Data

US 2011/0266133 A1 Nov. 3, 2011

Related U.S. Application Data

(60) Provisional application No. 61/329,768, filed on Apr. 30, 2010.

(51) Int. Cl.
| | |
|---|---|
| C07C 51/02 | (2006.01) |
| C07C 55/14 | (2006.01) |
| C07C 51/43 | (2006.01) |
| B01D 3/14 | (2006.01) |
| B01D 3/34 | (2006.01) |
| B01D 9/00 | (2006.01) |
| C07C 51/46 | (2006.01) |
| C07C 51/44 | (2006.01) |

(52) U.S. Cl.
CPC ............... *C07C 51/02* (2013.01); *C07C 51/46* (2013.01); *C07C 51/43* (2013.01); *C07C 51/44* (2013.01)
USPC .............. 562/593; 203/6; 203/47; 203/48; 203/50; 203/71; 562/590

(58) Field of Classification Search
USPC ............... 203/6, 47, 48, 50, 71; 562/590, 593
See application file for complete search history.

(56) References Cited

U.S. PATENT DOCUMENTS

| | | | |
|---|---|---|---|
| 2,288,687 | A | 7/1942 | Dreyfus |
| 2,912,363 | A | 11/1959 | La Roe |

(Continued)

FOREIGN PATENT DOCUMENTS

| | | |
|---|---|---|
| CA | 999013 | 10/1966 |
| DE | 1 904 613 A1 | 9/1969 |

(Continued)

OTHER PUBLICATIONS

Coulson et al Chemical Engineering , vol. Two, Unit operations, Third Ed.(1977), p. 478.*

(Continued)

*Primary Examiner* — Virginia Manoharan
(74) *Attorney, Agent, or Firm* — Paula DeGrandis

(57) ABSTRACT

A process for making MAA from a clarified DAA-containing fermentation broth includes (a) distilling the broth to form an overhead that includes water and ammonia, and a liquid bottoms that includes MAA, at least some DAA, and at least about 20 wt. % water; (b) cooling the bottoms to a temperature sufficient to cause the bottoms to separate into a DAA-containing liquid portion in contact with a MAA-containing solid portion that is substantially free of DAA; (c) separating the solid portion from the liquid portion; and (d) recovering the solid portion.

24 Claims, 3 Drawing Sheets

(56) References Cited

U.S. PATENT DOCUMENTS

| | | | |
|---|---|---|---|
| 3,063,910 A | 11/1962 | Abe et al. | |
| 3,433,830 A | 3/1969 | Wilkes | |
| 3,661,995 A | 5/1972 | Waddan et al. | |
| 3,671,566 A | 6/1972 | Decker et al. | |
| 3,873,425 A | 3/1975 | Kobayashi et al. | |
| 4,052,441 A * | 10/1977 | Brunner | 560/179 |
| 4,082,788 A * | 4/1978 | Mims | 558/443 |
| 4,105,856 A * | 8/1978 | Newton | 560/191 |
| 4,238,603 A | 12/1980 | Chapman et al. | |
| 4,254,283 A | 3/1981 | Mock | |
| 4,271,315 A * | 6/1981 | Cywinski | 560/204 |
| 4,339,536 A | 7/1982 | Kato et al. | |
| 4,400,468 A | 8/1983 | Faber | |
| 4,480,034 A | 10/1984 | Hsieh | |
| 4,535,059 A | 8/1985 | Hsieh et al. | |
| 4,540,772 A | 9/1985 | Pipper et al. | |
| 4,564,594 A | 1/1986 | Goldberg et al. | |
| 5,109,104 A | 4/1992 | Marks | |
| 5,151,543 A | 9/1992 | Ziemechki | |
| 5,231,016 A | 7/1993 | Cros et al. | |
| 5,352,825 A * | 10/1994 | Felman et al. | 562/580 |
| 5,457,040 A | 10/1995 | Jarry et al. | |
| 5,487,987 A | 1/1996 | Frost et al. | |
| 5,616,496 A | 4/1997 | Frost et al. | |
| 5,824,820 A | 10/1998 | Alas | |
| 6,238,896 B1 | 5/2001 | Ozaki et al. | |
| 6,794,165 B2 | 9/2004 | Cheng et al. | |
| 6,825,379 B2 * | 11/2004 | Chou et al. | 562/524 |
| 6,958,381 B2 | 10/2005 | Winterling et al. | |
| 7,132,562 B2 | 11/2006 | Allgeier | |
| 2008/0060948 A1 | 3/2008 | Goetheer et al. | |
| 2009/0305364 A1 | 12/2009 | Burgard et al. | |

FOREIGN PATENT DOCUMENTS

| | | |
|---|---|---|
| DE | 1 916 601 A1 | 10/1970 |
| DE | 27 18 363 A1 | 10/1973 |
| DE | 2 639002 A1 | 3/1978 |
| DE | 2 729 421 A1 | 1/1979 |
| EP | 0129196 A2 | 12/1984 |
| GB | 532938 A | 2/1941 |
| GB | 778253 A | 7/1957 |
| GB | 1050639 A1 | 7/1957 |
| WO | 00/24808 A1 | 5/2000 |
| WO | 2009/113853 | 9/2009 |
| WO | 2010/003728 A1 | 1/2010 |

OTHER PUBLICATIONS

Niu, W. et al., "Benzene-Free Synthesis of Adipic Acid," *Biotechol. Prog.*, 2002, vol. 18, No. 2, pp. 201-211.

McMaster, L., "The Preperation and Properties of the Neutral Ammonium Salts of Organic Acids," *Journal of the American Chemical Society*. 1914, vol. 36, pp. 742-747.

Okuhara, M. et al., "Formation of Glutaric and Adipic Acids from n-Alkanes with Odd and Even Numbers of Carbons by *Candida tropicalis* OH23," *Agr. Biol. Chem.*, 1971, vol. 35, No. 9, pp. 1376-1380.

Draths, K.M. et al., "Environmentally Compatible Synthesis of Adipic Acid from D-Glucose," *J. Am. Chem. Soc.*, 1994, vol. 116, pp. 399-400 (printout—1 sheet).

Draths, K.M. et al., "Benzene-Free Synthesis of Adipic Acid," *Biotechnol. Prog.*, Mar.-Apr. 2002, vol. 18, No. 2, pp. 201-211 (Abstract—1 sheet).

Kaneyuki, H. et al., "Production of Sebacic Acid from n-Decane by Mutants from *Torulopsis candida*," *J. Ferment. Technol.*, 1980, vol. 58, No. 5, pp. 405-410.

Ulezlo IV, R. "Search for Yeast Producers of Brassylic and Sebacic Fatty Acids," *Prikl Biokhim Mikrobiol.*, Sep.-Oct. 2004, vol. 40, No. 5, pp. 533-535 (English translation of Abstract—1 page).

Gomi, K. et al., "Purification and Characterization of Pyrocatechase from the Catechol-Assimilating Yeast *Candida Maliosa*,"*Agri. Biol. Chem.*, 1988, vol. 52, No. 2, pp. 585-587.

Ohusgi, M. et al., "Pimelic Acid as a Degradation Product of Azelaic Acid by Yeasts," *Agric. Biol. Chem.*, 1984, vol. 48, No. 7, pp. 1881-1882.

Vavra, J.J. et al., "Aerobic and Anaerobic Biosynthesis of Amino Acides by Bakers' Yeast," Published by *The Department of Biochemistry, College of Agriculture, University of Wisconsin*, 1955, pp. 33-43.

Mattoon, J.R. et al., "Glutaric Acid Accumulation by a Lysine-Requiring Yeast Mutant," *The Journal of Biological Chemistry*, Nov. 1962, vol. 237, No. 11, pp. 3486-3490.

Roa Engel, C.A. et al., "Fumaric Acid Production by Fermentation," *Appl. Microbiol. Biotechnol.*, 2008, vol. 78, pp. 379-389.

Bonnarme, P. et al., "Itaconate Biosynthesis in *Aspergilus terreus*,"*Journal of Bacteriology*, Jun. 1995, vol. 177, No. 12, pp. 3573-3578.

Diwarti, L. et al., "Itaconic Acid Production Using Sago Starch Hydrolysate by *Aspergilus terreus* TN484-M1," *Bioresour Technol.*, Dec. 2007, vol. 98, No. 17, pp. 3329-3337 (English translation of Abstract—1 sheet).

Lai, L.S. et al., "Effect of lactose and Glucose on Production of Itaconic Acid and Lovastatin by *Aspergilus terreus* ATTCC 20542," *J Biosci Bioeng.*, Jul. 2007, vol. 104, No. 1, pp. 9-13 (English translation of Abstract—1 sheet).

Magnuson, J.K. et al., "Organic Acid Production by Filamentous Fungi," *Advances in Fungal Biotechnology for Industry, Agriculture, and Medicine*, 2004, pp. 307-340.

Challener, C., "Au naturel—Rising Petrochemical Prices and Growing Interests in More Sustainable Processes Have Led Many Fine and Speciality Chemical Companies to Look to Renewable Resources for Raw Materials," *Speciality Chemicals Magazine*, Oct. 2006, cover and 5 pages.

"National Laboratory Field Work Proposal—Final Report," *Pacific Northwest national Laboratory*, Aug. 15, 2002, 5 pages.

"Verdezyne Produces Adipic Acid Biologically," *Verdezyne*, 2010, 2 pages.

"ATCC® Number: 98014," *ATCC—The Global Bioresouce Center—Search Catalog*, website printout http://www.atcc.org/ATCCAdvancedCatalogSearch/ProductDetails/Tabid/452/Default.aspx?ATCCNum=... dated Mar. 30, 2010, 2 pages.

"ATCC® Number: 24887™," *ATCC—The Global Bioresouce Center—Search Catalog*, website printout http://www.atcc.org/ATCCAdvancedCatalogSearch/ProductDetails/tabid/452/Default.aspx?ATCCNum=... dated Mar. 30, 2010, 2 pages.

* cited by examiner

SEQUENCE LISTING

<160> NUMBER OF SEQ ID NOS: 2

<210> SEQ ID NO 1
<211> LENGTH: 1644
<212> TYPE: DNA
<213> ORGANISM: Acinetobacter sp.

<400> SEQUENCE: 1

```
atggagatta tcatgtcaca aaaaatggat tttgatgcta tcgtgattgg tggtggtttt      60
ggcggacttt atgcagtcaa aaaattaaga gacgagctcg aacttaaggt tcaggctttt     120
gataaagcca cggatgtcgc aggtacttgg tactggaacc gttacccagg tgcattgtcg     180
gatacagaaa cccacctcta ctgctattct tgggataaag aattactaca atcgctagaa     240
atcaagaaaa aatatgtgca aggccctgat gtacgcaagt atttacagca agtggctgaa     300
aagcatgatt taaagaagag ctatcaattc aataccgcgg ttcaatcggc tcattacaac     360
gaagcagatg ccttgtggga agtcaccact gaatatggtg ataagtacac ggcgcgtttc     420
ctcatcactg ctttaggctt attgtctgcg cctaacttgc caaacatcaa aggcattaat     480
cagtttaaag gtgagctgca tcataccagc cgctggccag atgacgtaag ttttgaaggt     540
aaacgtgtcg gcgtgattgg tacgggttcc accggtgttc aggttattac ggctgtggca     600
cctctggcta aacacctcac tgtcttccag cgttctgcac aatacagcgt tccaattggc     660
aatgatccac tgtctgaaga agatgttaaa aagatcaaag acaattatga caaaatttgg     720
gatggtgtat ggaattcagc ccttgccttt ggcctgaatg aaagcacagt gccagcaatg     780
agcgtatcag ctgaagaacg caaggcagtt tttgaaaagg catggcaaac aggtggcggt     840
ttccgtttca tgtttgaaac tttcggtgat attgccacca atatggaagc caatatcgaa     900
gcgcaaaatt tcattaaggg taaaattgct gaaatcgtca aagatccagc cattgcacag     960
aagcttatgc cacaggattt gtatgcaaaa cgtccgttgt gtgacagtgg ttactacaac    1020
acctttaacc gtgacaatgt ccgtttagaa gatgtgaaag ccaatccgat tgttgaaatt    1080
accgaaaacg gtgtgaaact cgaaaatggc gatttcgttg aattagacat gctgatatgt    1140
gccacaggtt ttgatgccgt cgatggcaac tatgtgcgca tggacattca aggtaaaaac    1200
ggcttggcca tgaaagacta ctggaagaa ggtccgtcga gctatatggg tgtcaccgta    1260
aataactatc caaacatgtt catggtgctt ggaccgaatg gcccgtttac caacctgccg    1320
ccatcaattg aatcacaggt ggaatggatc agtgatacca tcaatacac ggttgaaaac    1380
aatgttgaat ccattgaagc gacaaaagaa gcggaagaac aatggactca aacttgcgcc    1440
aatattgcgg aaatgacctt attccctaaa gcgcaatcct ggatttttgg tgcgaatatc    1500
ccgggcaaga aaaacacggt ttacttctat ctcggtggtt taaaagaata tcgcagtgcg    1560
ctagccaact gcaaaaacca tgcctatgaa ggttttgata ttcaattaca acgttcagat    1620
atcaagcaac tgccaatgc ctaa                                            1644
```

<210> SEQ ID NO 2
<211> LENGTH: 547
<212> TYPE: PRT

<213> ORGANISM: Acinetobacter sp.

<400> SEQUENCE: 2

```
Met Glu Ile Ile Met Ser Gln Lys Met Asp Phe Asp Ala Ile Val Ile
1               5                   10                  15
Gly Gly Gly Phe Gly Gly Leu Tyr Ala Val Lys Lys Leu Arg Asp Glu
            20                  25                  30
Leu Glu Leu Lys Val Gln Ala Phe Asp Lys Ala Thr Asp Val Ala Gly
        35                  40                  45
Thr Trp Tyr Trp Asn Arg Tyr Pro Gly Ala Leu Ser Asp Thr Glu Thr
    50                  55                  60
His Leu Tyr Cys Tyr Ser Trp Asp Lys Glu Leu Gln Ser Leu Glu
65                  70                  75                  80
Ile Lys Lys Lys Tyr Val Gln Gly Pro Asp Val Arg Lys Tyr Leu Gln
                85                  90                  95
Gln Val Ala Glu Lys His Asp Leu Lys Lys Ser Tyr Gln Phe Asn Thr
            100                 105                 110
Ala Val Gln Ser Ala His Tyr Asn Glu Ala Asp Ala Leu Trp Glu Val
        115                 120                 125
Thr Thr Glu Tyr Gly Asp Lys Tyr Thr Ala Arg Phe Leu Ile Thr Ala
    130                 135                 140
Leu Gly Leu Leu Ser Ala Pro Asn Leu Pro Asn Ile Lys Gly Ile Asn
145                 150                 155                 160
Gln Phe Lys Gly Glu Leu His His Thr Ser Arg Trp Pro Asp Asp Val
                165                 170                 175
Ser Phe Glu Gly Lys Arg Val Gly Val Ile Gly Thr Gly Ser Thr Gly
            180                 185                 190
Val Gln Val Ile Thr Ala Val Ala Pro Leu Ala Lys His Leu Thr Val
        195                 200                 205
Phe Gln Arg Ser Ala Gln Tyr Ser Val Pro Ile Gly Asn Asp Pro Leu
    210                 215                 220
Ser Glu Glu Asp Val Lys Lys Ile Lys Asp Asn Tyr Asp Lys Ile Trp
225                 230                 235                 240
Asp Gly Val Trp Asn Ser Ala Leu Ala Phe Gly Leu Asn Glu Ser Thr
                245                 250                 255
Val Pro Ala Met Ser Val Ser Ala Glu Glu Arg Lys Ala Val Phe Glu
            260                 265                 270
Lys Ala Trp Gln Thr Gly Gly Gly Phe Arg Phe Met Phe Glu Thr Phe
        275                 280                 285
Gly Asp Ile Ala Thr Asn Met Glu Ala Asn Ile Glu Ala Gln Asn Phe
    290                 295                 300
Ile Lys Gly Lys Ile Ala Glu Ile Val Lys Asp Pro Ala Ile Ala Gln
305                 310                 315                 320
Lys Leu Met Pro Gln Asp Leu Tyr Ala Lys Arg Pro Leu Cys Asp Ser
                325                 330                 335
Gly Tyr Tyr Asn Thr Phe Asn Arg Asp Asn Val Arg Leu Glu Asp Val
            340                 345                 350
Lys Ala Asn Pro Ile Val Glu Ile Thr Glu Asn Gly Val Lys Leu Glu
        355                 360                 365
Asn Gly Asp Phe Val Glu Leu Asp Met Leu Ile Cys Ala Thr Gly Phe
    370                 375                 380
Asp Ala Val Asp Gly Asn Tyr Val Arg Met Asp Ile Gln Gly Lys Asn
385                 390                 395                 400
```

```
Gly Leu Ala Met Lys Asp Tyr Trp Lys Glu Gly Pro Ser Ser Tyr Met
            405                 410                 415
Gly Val Thr Val Asn Asn Tyr Pro Asn Met Phe Met Val Leu Gly Pro
            420                 425                 430
Asn Gly Pro Phe Thr Asn Leu Pro Pro Ser Ile Glu Ser Gln Val Glu
            435                 440                 445
Trp Ile Ser Asp Thr Ile Gln Tyr Thr Val Glu Asn Asn Val Glu Ser
        450                 455                 460
Ile Glu Ala Thr Lys Glu Ala Glu Glu Gln Trp Thr Gln Thr Cys Ala
465                 470                 475                 480
Asn Ile Ala Glu Met Thr Leu Phe Pro Lys Ala Gln Ser Trp Ile Phe
                485                 490                 495
Gly Ala Asn Ile Pro Gly Lys Lys Asn Thr Val Tyr Phe Tyr Leu Gly
            500                 505                 510
Gly Leu Lys Glu Tyr Arg Ser Ala Leu Ala Asn Cys Lys Asn His Ala
        515                 520                 525
Tyr Glu Gly Phe Asp Ile Gln Leu Gln Arg Ser Asp Ile Lys Gln Pro
    530                 535                 540
Ala Asn Ala
545
```

PROCESSES FOR PRODUCING MONOAMMONIUM ADIPATE AND CONVERSION OF MONOAMMONIUM ADIPATE TO ADIPIC ACID

RELATED APPLICATION

This application claims the benefit of U.S. Provisional Application No. 61/329,768, filed Apr. 30, 2010, the subject matter of which is hereby incorporated by reference

SEQUENCE LISTING

This application contains a Sequence Listing which has been submitted in ASCII format via EFS-Web and is hereby incorporated by reference in its entirety. The ASCII copy, created on Apr. 28, 2011, is named DNP10105.txt and is 7,568 bytes in size.

TECHNICAL FIELD

This disclosure relates to processes for the direct production of monoammonium adipate (MAA) from fermentation broths containing diammonium adipate (DAA), MAA and/or adipic acid (AA). It also relates to the conversion of the MAA so obtained to AA.

BACKGROUND

Certain carbonaceous products of sugar fermentation are seen as replacements for petroleum-derived materials for use as feedstocks for the manufacture of carbon-containing chemicals. One such product is MAA. Another such product is AA.

It would therefore be desirable to have a process for the direct production of substantially pure MAA from a DAA, MAA, and/or AA-containing fermentation broth.

SUMMARY

We provide such a process by economically producing high purity MAA from a clarified DAA-containing fermentation broth. We thus provide a process for making MAA from a clarified DAA-containing fermentation broth in which the DAA preferably constitutes at least 90 wt. % of the total diammonium dicarboxylate salts contained in the broth, including (a) distilling the broth to form an overhead that comprises water and ammonia, and a liquid bottoms that comprises MAA, at least some DAA, and at least about 20 wt. % water; (b) cooling and/or evaporating the bottoms, and optionally adding an antisolvent to the bottoms, to attain a temperature and composition sufficient to cause the bottoms to separate into a DAA-containing liquid portion and a MAA-containing solid portion that is substantially free of DAA; (c) separating the solid portion from the liquid portion; and (d) recovering the solid portion.

We also provide a process for making AA from a DAA-containing fermentation broth, including (a) distilling the broth to form a first overhead that includes water and ammonia, and a first liquid bottoms that includes MAA, at least some DAA, and at least about 20 wt. % water; (b) cooling and/or evaporating the bottoms, and optionally adding an antisolvent to the bottoms, to attain a temperature and composition sufficient to cause the bottoms to separate into a DAA-containing liquid portion and a MAA-containing solid portion that is substantially free of DAA; (c) separating the solid portion from the liquid portion; (d) recovering the solid portion; (e) dissolving the solid portion in water to produce an aqueous MAA solution; (f) distilling the aqueous MAA solution at a temperature and pressure sufficient to form a second overhead that includes water and ammonia, and a second bottoms that includes a major portion of AA, a minor portion of MAA, and water; (g) cooling and/or evaporating the second bottoms to cause the second bottoms to separate into a second liquid portion in contact with a second solid portion that preferably consists essentially of AA and is substantially free of MAA; (h) separating the second solid portion from the second liquid portion; and (i) recovering the second solid portion.

We further provide a process for making MAA from a clarified MAA-containing broth including (a) optionally, adding MAA, DAA, AA, $NH_3$, and/or $NH_4^+$ to the broth to preferably maintain the pH of the broth below 6; (b) distilling the broth to form an overhead that includes water and optionally ammonia, and a liquid bottoms that includes MAA, at least some DAA, and at least about 20 wt. % water; (c) cooling and/or evaporating the bottoms, and optionally adding an antisolvent to the bottoms, to attain a temperature and composition sufficient to cause the bottoms to separate into a DAA-containing liquid portion and a MAA-containing solid portion that is substantially free of DAA; (d) separating the solid portion from the liquid portion; and (e) recovering the solid portion.

We further yet provide a process for making AA from a clarified MAA-containing fermentation broth including (a) optionally, adding MAA, DAA, AA, $NH_3$, and/or $NH_4^+$ to the broth to preferably maintain the pH of the broth below 6; (b) distilling the broth to form an overhead that includes water and optionally ammonia, and a liquid bottoms that includes MAA, at least some DAA, and at least about 20 wt. % water; (c) cooling and/or evaporating the bottoms, and optionally adding an antisolvent to the bottoms, to attain a temperature and composition sufficient to cause the bottoms to separate into a DAA-containing liquid portion and a MAA-containing solid portion that is substantially free of DAA; (d) separating the solid portion from the liquid portion; (e) recovering the solid portion; (f) dissolving the solid portion in water to produce an aqueous MAA solution; (g) distilling the aqueous MAA solution at a temperature and pressure sufficient to form a second overhead that includes water and ammonia, and a second bottoms that includes a major portion of AA, a minor portion of MAA, and water; (h) cooling and/or evaporating the second bottoms to cause the second bottoms to separate into a second liquid portion in contact with a second solid portion that preferably consists essentially of AA and is substantially free of MAA; (i) separating the second solid portion from the second liquid portion; and (j) recovering the second solid portion.

We additionally provide processes for making MXA from a clarified DAA-containing fermentation broth. Salts of adipic acid in the DAA-containing fermentation broth are converted to MXA to derive MXA from the fermentation broth, where MXA is monosodium adipate (MNaA) when a sodium (Na) base is used, monopotassium adipate (MKA) when a potassium (K) base is used, or MAA when an ammonia ($NH_4^+$ or $NH_3$) base is used. The process thus includes (a) distilling the broth to form an overhead that comprises water and ammonia, and a liquid bottoms that comprises MXA, where X is at least one of $NH_4^+$, $Na^+$ and $K^+$, at least some DYA, where DYA includes DAA and at least one of disodium adipate (DNaA) and dipotassium adipate (DKA), and at least about 20 wt. % water; (b) cooling and/or evaporating the bottoms, and optionally adding an antisolvent to the bottoms, to attain a temperature and composition sufficient to cause the bottoms to separate into a DYA-containing liquid portion and a MXA-containing solid portion that is substantially free of DYA; (c) separating the solid portion from the liquid portion; and (d) recovering the solid portion.

We further additionally provide a process for making MXA from a clarified MXA-containing broth, where X is at least one of $NH_4^+$, $Na^+$ and $K^+$ including (a) optionally, adding at least one of AA, $NH_3$, $NH_4^+$, $Na^+$, and $K^+$ to the broth to preferably maintain the pH of the broth below 6; (b) distilling the broth to form an overhead that includes water and optionally ammonia, and a liquid bottoms that includes MXA, at least some DYA, where DYA includes at least one of DAA, DNaA and DKA, and at least about 20 wt. % water; (c) cooling and/or evaporating the bottoms, and optionally adding an antisolvent to the bottoms, to attain a temperature and composition sufficient to cause the bottoms to separate into a DYA-containing liquid portion and a MXA-containing solid portion that is substantially free of DYA; (d) separating the solid portion from the liquid portion; and (e) recovering the solid portion.

We also provide a process for making magnesium adipate (MgA) from a clarified DAA-containing fermentation broth including (a) distilling the broth to form an overhead that includes water and ammonia, and a liquid bottoms that includes MgA, at least some DAS and MgA and at least about 20 wt. % water; (b) cooling and/or evaporating the bottoms, and optionally adding an antisolvent to the bottoms, to attain a temperature and composition sufficient to cause the bottoms to separate into a DAA and MgA-containing liquid portion and an MgA-containing solid portion that is substantially free of DAA; (c) separating the solid portion from the liquid portion; and (d) recovering the solid portion.

We additionally provide a process for making MgA from a clarified MAA-containing fermentation broth including (a) optionally adding at least one of AA, $NH_3$, $NH_4^+$ and $Mg^{+2}$ to the broth depending on pH of the broth; (b) distilling the broth to form an overhead that comprises water and optionally ammonia and a liquid bottoms that comprises MgA, at least some MAA, and at least about 20 wt. % water; (c) cooling and/or evaporating the bottoms, and optionally adding an antisolvent to the bottoms, to attain a temperature and composition sufficient to cause the bottoms to separate into a MAA-containing liquid portion and a MgA-containing solid portion that is substantially free of MAA; (d) separating the solid portion from the liquid portion; and (e) recovering the solid portion.

DETAILED DESCRIPTION

Figure 1:
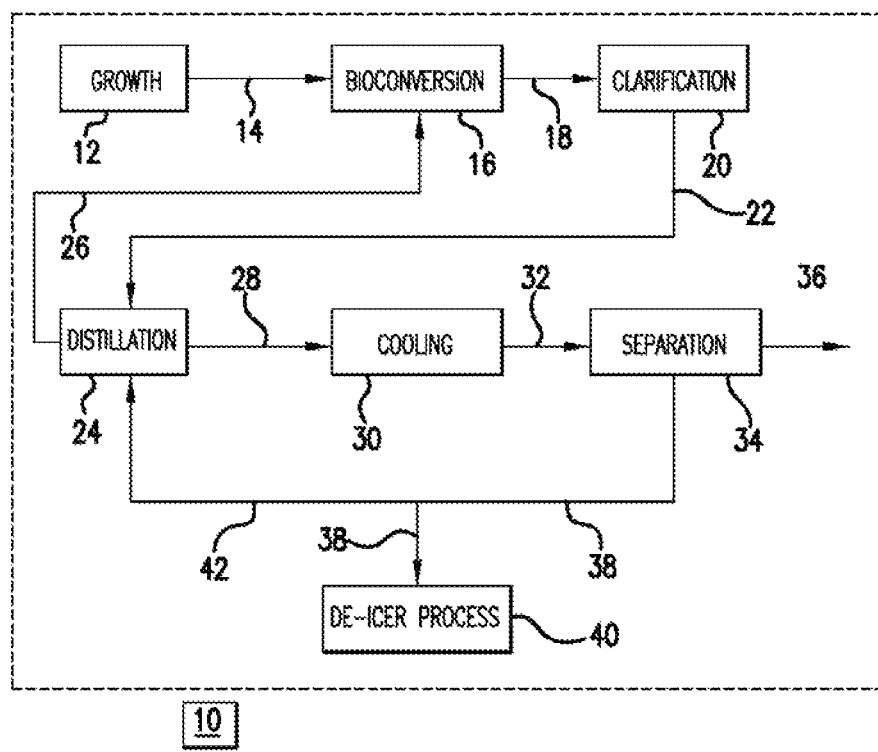
FIG. 1 is a block diagram of one example of a process for making MAA from a DAA containing broth.

It will be appreciated that at least a portion of the following description is intended to refer to representative examples of processes selected for illustration in the drawings and is not intended to define or limit the disclosure, other than in the appended claims.

Our processes may be appreciated by reference to FIG. 1, which shows in block diagram form one representative example 10 of our methods.

A growth vessel 12, typically an in-place steam sterilizable fermentor, may be used to grow a microbial culture (not shown) that is subsequently utilized for the production of the DAA, MAA, and/or AA-containing fermentation broth. Such growth vessels are known in the art and are not further discussed.

The microbial culture may comprise microorganisms capable of producing AA from fermentable carbon sources such as carbohydrate sugars (e.g., glucose), cyclohexanol, alkanes (e.g., n-alkanes) and plant based oils. Representative examples of microorganisms include *Escherichia coli* (*E. coli*), *Aspergillus niger*, *Corynebacterium glutamicum* (also called *Brevibacterium flavum*), *Enterococcus faecalis*, *Veillonella parvula*, *Actinobacillus succinogenes*, *Paecilomyces varioti*, *Saccharomyces cerevisiae*, *Candida tropicalis*, *Bacteroides fragilis*, *Bacteroides ruminicola*, *Bacteroides amylophilus*, *Klebsiella pneumoniae*, mixtures thereof and the like.

Preferred microorganisms may include the *Candida tropicalis* (Castellani) Berkhout, anamorph strain OH23 having ATCC accession number 24887, *E. coli* strain AB2834/pKD136/pKD8.243A/pKD8.292 having ATCC accession number 69875, the *E. coli* cosmid clones designated 5B12, 5F5, 8F6 and 14D7 comprising a vector expressing the cyclohexanone monoxygenase having the amino acid sequence shown in SEQ ID NO: 2 and encoded by SEQ ID NO: 1 from *Acinetobacter* strain SE19, and the yeast strain available from Verdezyne, Inc. (Carlsbad, Calif., USA; hereinafter "Verdezyne Yeast") which produces AA from alkanes and other carbon sources.

Fermentation broths containing AA can be produced from the *Candida tropicalis* (Castellani) Berkhout, anamorph strain OH23 having ATCC accession number 24887 by culture at 32° C. in a liquid medium containing 300 mg of $NH_4H_2PO_4$, 200 mg of $KH_2PO_4$, 100 mg of $K_2HPO_4$, 50 mg of $MgSO_4.7H_2O$, 1 µg of biotin, 0.1% (w/v) yeast extract and about 1% (v/v) n-hexadecane in 100 ml of distilled water. Other culture media such as YM broth containing n-hexadecane may also be used. The procedure for producing fermentation broths containing AA from media containing n-hexadecane by culturing *Candida tropicalis* (Castellani) Berkhout, anamorph strain OH23 having ATCC accession number 24887 is also described in Okuhura et al., 35 *Agr. Biol. Chem.* 1376 (1971), the subject matter of which is incorporated herein by reference.

Fermentation broths containing AA can also be produced from *E. coli* strain AB2834/pKD136/pKD8.243A/pKD8.292 having ATCC accession number 69875. This can be performed as follows. One liter of LB medium (in 4 L Erlenmeyer shake flask) containing IPTG (0.2 mM), ampicillin (0.05 g), chloramphenicol (0.02 g) and spectinomycin (0.05 g) can be inoculated with 10 mL of an overnight culture of *E. coli* strain AB2834/pKD136/pKD8.243A/pKD8.292 cells grown at 250 rpm for 10 h at 37° C. The cells can be harvested, resuspended in 1 L of M9 minimal medium containing 56 mM D-glucose, shikimic acid (0.04 g), IPTG (0.2 mM), ampicillin (0.05 g), chloramphenicol (0.02 g) and spectinomycin (0.05 g). The cultures can then be returned to 37° C. incubation. After resuspension in minimal medium the pH of the culture can be closely monitored, particularly over the initial 12 h. When the culture reaches a pH of 6.5, 5N NaOH or an appropriate amount of another base such as ammonium hydroxide can be added to adjust the pH back to approximately 6.8. Over the 48 h accumulation period, the culture should not allowed to fall below pH 6.3. After 24 h in the medium 12 mM cis,cis-muconate and 1 mM protocatechuate may be detected in the culture supernatant along with 23 mM D-glucose. After 48 h in the medium *E. coli* strain AB2834/pKD136/pKD8.243A/pKD8.292 cells can essentially replace the 56 mM D-glucose in the medium with 17 mM cis,cis-muconate.

The reduction of microbially synthesized cis,cis-muconate AA to produce a fermentation broth containing AA can then proceed as follows. Fifty milligrams of platinum on carbon (10%) can be added to 6 mL of a cell-free culture supernatant from the fermentation containing about 17.2 mM cis,cis-muconate. This sample can then be hydrogenated at 50 psi hydrogen pressure for 3 h at room temperature to produce a fermentation broth containing AA. The fermentation broth produced may contain, for example, about 15.1 mM AA. The procedure for producing fermentation broths containing AA by culturing *E. coli* strain AB2834/pKD136/pKD8.243A/pKD8.292 cells by culture in a growth medium comprising D-glucose is also described in Draths & Frost, 116 *J. Am. Chem. Soc.* 399 (1994); Draths and Frost, 18 *Biotechnol. Prog.* 201 (2002); U.S. Pat. No. 5,487,987 and U.S. Pat. No. 5,616,496, the subject matter of which is incorporated herein by reference.

Fermentation broths containing AA can also be produced from the *E. coli* cosmid clones designated 5B12, 5F5, 8F6 and 14D7 comprising a vector expressing the cyclohexanone monooxygenase SEQ ID NO: 2 encoded by SEQ ID NO: 1 from *Acinetobacter* strain SE19 by culturing these clones in M9 minimal medium supplemented with 0.4% glucose as the carbon source. Cells can be grown at 30° C. with shaking for 2 h and the addition of 330 ppm of cyclohexanol to the medium. This can be followed by further incubation at 30° C. for an additional period of time such as, for example, 2 h, 4 h or 20 h or other time intervals. The procedure for producing fermentation broths containing AA by culturing the *E. coli* cosmid clones designated 5B12, 5F5, 8F6 and 14D7 comprising a vector expressing the cyclohexanone monooxygenase encoded by SEQ ID NO: 1 from *Acinetobacter* strain SE19 in a growth medium comprising D-glucose and cyclohexanol is also described in U.S. Pat. No. 6,794,165, the subject matter of which is incorporated herein by reference.

Fermentation broths containing AA can also be produced with the Verdezyne Yeast strain available from Verdezyne, Inc. (Carlsbad, Calif., USA) which was reported on Feb. 8, 2010 to produce AA when cultured in a medium (e.g., SD medium) comprising alkanes or other carbon sources such as sugars and plant-based oils.

Fermentation broths containing AA can also be produced from *E. coli* or other microorganisms transformed with nucleic acids encoding succinyl-CoA:acetyl-CoA acyl transferase; 3-hydroxyacyl-CoA dehydrogenase; 3-hydroxyadipyl-CoA dehydratase; 5-carboxy-2-pentenoyl-CoA reductase; adipyl-CoA synthetase, phosphotransadipylase/adipate kinase, adipyl-CoA transferase or adipyl-CoA hydrolase. Fermentation broths containing AA can also be produced from *E. coli* or other microorganisms transformed with nucleic acids encoding succinyl-CoA:acetyl-CoA acyl transferase; 3-oxoadipyl-CoA transferase; 3-oxoadipate reductase; 3-hydroxyadipate dehydratase; and 2-enoate reductase. Fermentation broths containing AA can further be produced from *E. coli* or other microorganisms transformed with nucleic acids encoding alpha-ketoadipyl-CoA synthetase, phosphotransketoadipylase/alpha-ketoadipate kinase or alpha-ketoadipyl-CoA:acetyl-CoA tranferase; 2-hydroxyadipyl-CoA dehydrogenase; 2-hydroxyadipyl-CoA dehydratase; 5-carboxy-2-pentenoyl-CoA reductase; and adipyl-CoA synthetase, phosphotransadipylase/adipate kinase, adipyl-CoA:acetyl-CoA transferase or adipyl-CoA hydrolase. Fermentation broths containing AA can still further be produced from *E. coli* or other microorganisms transformed with nucleic acids encoding 2-hydroxyadipate dehydrogenase; 2-hydroxyadipyl-CoA synthetase, phosphotranshydroxyadipylase/2-hydroxyadipate kinase or 2-hydroxyadipyl-CoA:acetyl-CoA transferase; 2-hydroxyadipyl-CoA dehydratase; 5-carboxy-2-pentenoyl-CoA reductase; and adipyl-CoA synthetase, phosphotransadipylase/adipate kinase, adipyl-CoA:acetyl-CoA transferase or adipyl-CoA hydrolase.

Fermentations with *E. coli* or other microorganisms transformed with nucleic acids encoding these enzymes may be performed using a variety of different carbon sources under standard conditions in standard culture mediums (e.g., M9 minimal medium) and appropriate antibiotic or nutritional supplements to maintain the transformed phenotype. The procedure for producing fermentation broths containing AA by culturing *E. coli* or other microorganisms transformed with nucleic acids encoding these enzymes, appropriate growth mediums and carbon sources are also described in US 2009/0305364, the subject matter of which is incorporated herein by reference.

Procedures for producing fermentation broths containing dicarboxylic acids such as AA by culturing *Saccharomyces cerevisiae* strains, and other microorganism strains, appropriate growth mediums and carbon sources are also described in WO 2010/003728, the subject matter of which is incorporated herein by reference.

A fermentable carbon source (e.g., carbohydrates and sugars), optionally a source of nitrogen and complex nutrients (e.g., corn steep liquor), additional media components such as vitamins, salts and other materials that can improve cellular growth and/or product formation, and water may be fed to the growth vessel 12 for growth and sustenance of the microbial culture. Typically, the microbial culture is grown under aerobic conditions provided by sparging an oxygen-rich gas (e.g., air or the like). Typically, an acid (e.g., sulphuric acid or the like) and ammonium hydroxide are provided for pH control during the growth of the microbial culture.

In one example (not shown), the aerobic conditions in growth vessel 12 (provided by sparging an oxygen-rich gas) are switched to anaerobic conditions by changing the oxygen-rich gas to an oxygen-deficient gas (e.g., $CO_2$ or the like). The anaerobic environment may trigger bioconversion of the fermentable carbon source to AA in situ in growth vessel 12. Ammonium hydroxide may be provided for pH control during bioconversion of the fermentable carbon source to AA. The produced AA is at least partially neutralized to DAA due to the presence of the ammonium hydroxide, leading to the production of a broth comprising DAA. The $CO_2$ may provide an additional source of carbon for the production of AA.

In another example, the contents of growth vessel 12 may be transferred via stream 14 to a separate bioconversion vessel 16 for bioconversion of a carbohydrate source to AA. An oxygen-deficient gas (e.g., $CO_2$ or the like) may be sparged in bioconversion vessel 16 to provide anaerobic conditions that trigger production of AA. Ammonium hydroxide is provided for pH control during bioconversion of the carbohydrate source to AA. Due to the presence of the ammonium hydroxide, the AA produced is at least partially neutralized to DAA, leading to production of a broth that comprises DAA. The $CO_2$ may provide an additional source of carbon for production of AA.

In another example, the bioconversion may be conducted at relatively low pH (e.g., 3 to 6). A base (ammonium hydroxide or ammonia) may be provided for pH control during bioconversion of the carbohydrate source to AA. Depending of the desired pH, due to the presence or lack of the ammonium hydroxide, either AA is produced or the AA produced is at least partially neutralized to MAA, DAA, or a mixture comprising AA, MAA and/or DAA. Thus, the AA produced during bioconversion can be subsequently neutralized, optionally in an additional step, by providing either ammonia or ammonium hydroxide leading to a broth comprising DAA. As a consequence, a "DAA-containing fermentation broth" generally means that the fermentation broth comprises DAA and possibly any number of other components such as MAA and/or AA, whether added and/or produced by bioconversion or otherwise. Similarly, a "MAA-containing fermentation broth" generally means that the fermentation broth comprises MAA and possibly any number of other components such as DAA and/or AA, whether added and/or produced by bioconversion or otherwise.

The broth resulting from the bioconversion of the fermentable carbon source (in either growth vessel 12 or bioconversion vessel 16, depending on where the bioconversion takes place), typically contains insoluble solids such as cellular biomass and other suspended material, which are transferred via stream 18 to clarification apparatus 20 before distillation. Removal of insoluble solids clarifies the broth. This reduces or prevents fouling of subsequent distillation equipment. The insoluble solids can be removed by any one of several solid-liquid separation techniques, alone or in combination, including but not limited to centrifugation and filtration (including, but not limited to ultra-filtration, micro-filtration or depth filtration). The choice of filtration technique can be made using techniques known in the art. Soluble inorganic compounds can be removed by any number of known methods such as, but not limited to, ion exchange and physical adsorption.

An example of centrifugation is a continuous disc stack centrifuge. It may be useful to add a polishing filtration step following centrifugation such as dead-end or cross-flow filtration, which may include the use of a filter aide such as diatomaceous earth or the like, or more preferably ultra-filtration or micro-filtration. The ultra-filtration or micro-filtration membrane can be ceramic or polymeric, for example. One example of a polymeric membrane is SelRO MPS-U20P (pH stable ultra-filtration membrane) manufactured by Koch Membrane Systems (850 Main Street, Wilmington, Mass., USA). This is a commercially available polyethersulfone membrane with a 25,000 Dalton molecular weight cut-off which typically operates at pressures of 0.35 to 1.38 MPa (maximum pressure of 1.55 MPa) and at temperatures up to 50° C. Alternatively, a filtration step may be employed, such as ultra-filtration or micro-filtration alone.

The resulting clarified DAA-containing broth, substantially free of the microbial culture and other solids, is transferred via stream 22 to distillation apparatus 24.

The clarified distillation broth should contain DAA and/or MAA in an amount that is at least a majority of, preferably at least about 70 wt. %, more preferably 80 wt. % and most preferably at least about 90 wt. % of all the diammonium dicarboxylate salts in the broth. The concentration of DAA and/or MAA as a weight percent (wt. %) of the total dicarboxylic acid salts in the fermentation broth can be easily determined by high pressure liquid chromatography (HPLC) or other known means.

Water and ammonia are removed from distillation apparatus 24 as an overhead, and at least a portion is optionally recycled via stream 26 to bioconversion vessel 16 (or growth vessel 12 operated in the anaerobic mode). Specific distillation temperature and pressure may not be critical as long as the distillation is carried out in a way that ensures that the distillation overhead contains water and ammonia, and the distillation bottoms comprises at least some DAA and at least about 20 wt. % water. A more preferred amount of water is at least about 30 wt. % and an even more preferred amount is at least about 40 wt. %. The rate of ammonia removal from the distillation step increases with increasing temperature and also can be increased by injecting steam (not shown) during distillation. The rate of ammonia removal during distillation may also be increased by conducting distillation under a vacuum or by sparging the distillation apparatus with a non-reactive gas such as air, nitrogen or the like.

Removal of water during the distillation step can be enhanced by the use of an organic azeotroping agent such as toluene, xylene, hexane, cyclohexane, methyl cyclohexane, methyl isobutyl ketone, heptane or the like, provided that the bottoms contains at least about 20 wt. % water. If the distillation is carried out in the presence of an organic agent capable of forming an azeotrope consisting of the water and the agent, distillation produces a biphasic bottoms that comprises an aqueous phase and an organic phase, in which case the aqueous phase can be separated from the organic phase, and the aqueous phase used as the distillation bottoms. By-products such as adipamide and adipimide are substantially avoided provided the water level in the bottoms is maintained at a level of at least about 30 wt. %.

A preferred temperature for the distillation step is in the range of about 50 to about 300° C., depending on the pressure. A more preferred temperature range is about 90 to about 150° C. A distillation temperature of about 110° C. to about 140° C. is preferred. "Distillation temperature" refers to the temperature of the bottoms (for batch distillations this may be the temperature at the time when the last desired amount of overhead is taken).

Adding a water miscible organic solvent or an ammonia separating solvent facilitates deammoniation over a variety of distillation temperatures and pressures as discussed above. Such solvents include aprotic, bipolar, oxygen-containing solvents that may be able to form passive hydrogen bonds. Examples include, but are not limited to, diglyme, triglyme, tetraglyme, sulfoxides such as dimethylsulfoxide (DMSO), amides such as dimethylformamide (DMF) and dimethylacetamide, sulfones such as dimethylsulfone, sulfolane, polyethyleneglycol (PEG), butoxytriglycol, N-methylpyrolidone (NMP), ethers such as dioxane, methyl ethyl ketone (MEK) and the like. Such solvents aid in the removal of ammonia from the DAA or MAA in the clarified broth. Regardless of the distillation technique, it is important that the distillation be carried out in a way that ensures that at least some DAA and at least about 20 wt. % water remain in the bottoms and even more advantageously at least about 30 wt. %.

The distillation can be performed at atmospheric, sub-atmospheric or super-atmospheric pressures. The distillation can be a one-stage flash, a multistage distillation (i.e., a multistage column distillation) or the like. The one-stage flash can be conducted in any type of flasher (e.g., a wiped film evaporator, thin film evaporator, thermosiphon flasher, forced circulation flasher and the like). The multistages of the distillation column can be achieved by using trays, packing or the like. The packing can be random packing (e.g., Raschig rings, Pall rings, Berl saddles and the like) or structured packing (e.g., Koch-Sulzer packing, Intalox packing, Mellapak and the like). The trays can be of any design (e.g., sieve trays, valve trays, bubble-cap trays and the like). The distillation can be performed with any number of theoretical stages.

If the distillation apparatus is a column, the configuration is not particularly critical, and the column can be designed using well known criteria. The column can be operated in either stripping mode, rectifying mode or fractionation mode. Distillation can be conducted in either batch or continuous mode. In the continuous mode, the broth is fed continuously into the distillation apparatus, and the overhead and bottoms are continuously removed from the apparatus as they are formed. The distillate from distillation is an ammonia/water solution, and the distillation bottoms is a liquid, aqueous solution of MAA and DAA, which may also contain other fermentation by-product salts (i.e., ammonium acetate, ammonium formate, ammonium lactate and the like) and color bodies.

The distillation bottoms can be transferred via stream 28 to cooling apparatus 30 and cooled by conventional techniques. Cooling technique is not critical. A heat exchanger (with heat recovery) can be used. A flash vaporization cooler can be used to cool the bottoms down to about 15° C. Cooling below 15° C. typically involves a refrigerated coolant such as, for example, glycol solution or, less preferably, brine. A concentration step can be included prior to cooling to help increase product yield. Further, both concentration and cooling can be combined using methods known such as vacuum evaporation and heat removal using integrated cooling jackets and/or external heat exchangers.

Figure 2:
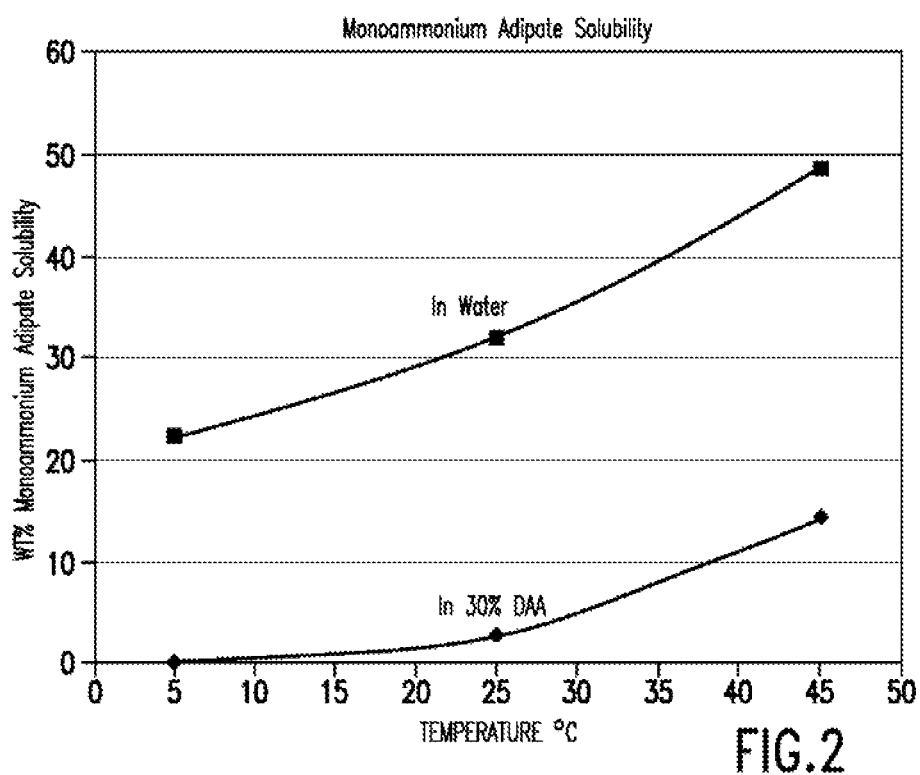
FIG. 2 is a graph showing the solubility of MAA as a function of temperature in both water and a 30% aqueous DAA solution.

We found that the presence of some DAA in the liquid bottoms facilitates cooling-induced separation of the bottoms into a liquid portion in contact with a solid portion that at least "consists essentially" of MAA (meaning that the solid portion is at least substantially pure crystalline MAA) by reducing the solubility of MAA in the liquid, aqueous, DAA-containing bottoms. FIG. 2 illustrates the reduced solubility of MAA in an aqueous 30 wt. % DAA solution at various temperatures ranging from 0° C. to 60° C. The upper curve shows that even at 0° C. MAA remains significantly soluble in water (i.e., about 20 wt. % in aqueous solution). The lower curve shows that at 0° C. MAA is essentially insoluble in a 30 wt. % aqueous DAA solution. We discovered, therefore, that MAA can be more completely crystallized out of an aqueous solution if some DAA is also present in that solution. A preferred concentration of DAA in such a solution is about 30 wt. %. A more preferred concentration of DAA in such a solution is in the ppm to about 3 wt. % range. This allows crystallization of MAA (i.e., formation of the solid portion of the distillation bottoms) at temperatures higher than those that would be required in the absence of DAA.

When about 50% of the ammonia is removed from DAA contained in an aqueous medium the adipate species establish an equilibrium molar distribution that is about 0.2:0.6:0.2 in DAA:MAA:AA within a pH range of 4.9 to 5.1, depending on the operating temperature and pressure. When this composition is concentrated and cooled, MAA exceeds its solubility limit in water and crystallizes. When MAA undergoes a phase change to the solid phase, the liquid phase equilibrium resets thereby producing more MAA (DAA donates an ammonium ion to AA). This causes more MAA to crystallize from solution and continues until appreciable quantities of AA are exhausted and the pH tends to rise. As the pH rises, the liquid phase distribution favors DAA. However, since DAA is highly soluble in water, MAA continues to crystallize as its solubility is lower than DAA. In effect, the liquid phase equilibrium and the liquid-solid equilibria of adipate species act as a "pump" for MAA crystallization, thereby enabling MAA crystallization in high yield.

In addition to cooling, evaporation, or evaporative cooling described above, crystallization of MAA can be enabled and/or facilitated by addition of an antisolvent. In this context, antisolvents may be solvents typically miscible with water, but cause crystallization of a water soluble salt such as MAA due to lower solubility of the salt in the solvent. Solvents with an antisolvent effect on MAA can be alcohols such as ethanol and propanol, ketones such as methyl ethyl ketone, ethers such as tetrahydrofuran and the like. The use of antisolvents is known and can be used in combination with cooling and evaporation or separately.

The distillation bottoms, after cooling in unit 30, is fed via stream 32 to separator 34 for separation of the solid portion from the liquid portion. Separation can be accomplished via pressure filtration (e.g., using Nutsche or Rosenmond type pressure filters), centrifugation and the like. The resulting solid product can be recovered as product 36 and dried, if desired, by standard methods.

After separation, it may be desirable to treat the solid portion to ensure that no liquid portion remains on the surface(s) of the solid portion. One way to minimize the amount of liquid portion that remains on the surface of the solid portion is to wash the separated solid portion with water and dry the resulting washed solid portion (not shown). A convenient way to wash the solid portion is to use a so-called "basket centrifuge" (not shown). Suitable basket centrifuges are available from The Western States Machine Company (Hamilton, Ohio, USA).

The liquid portion of the separator 34 (i.e., the mother liquor) may contain remaining dissolved MAA, any unconverted DAA, any fermentation by-products such as ammonium acetate, lactate, or formate, and other minor impurities. This liquid portion can be fed via stream 38 to a downstream apparatus 40. In one instance, apparatus 40 may be a means for making a de-icer by treating the mixture with an appropriate amount of potassium hydroxide, for example, to convert the ammonium salts to potassium salts. Ammonia generated in this reaction can be recovered for reuse in the bioconversion vessel 16 (or growth vessel 12 operating in the anaerobic mode). The resulting mixture of potassium salts is valuable as a de-icer and anti-icer.

The mother liquor from the solids separation step 34, can be recycled (or partially recycled) to distillation apparatus 24 via stream 42 to further enhance recovery of MAA, as well as further convert DAA to MAA.

The solid portion of the cooling-induced crystallization is substantially pure MAA and is, therefore, useful for the known utilities of MAA.

HPLC can be used to detect the presence of nitrogen-containing impurities such as adipamide and adipimide. The purity of MAA can be determined by elemental carbon and nitrogen analysis. An ammonia electrode can be used to determine a crude approximation of MAA purity.

Depending on the circumstances and various operating inputs, there are instances when the fermentation broth may be a clarified MAA-containing fermentation broth or a clarified AA-containing fermentation broth. In those circumstances, it can be advantageous to add MAA, DAA and/or AA to those fermentation broths to facilitate the production of substantially pure MAA. For example, the operating pH of the fermentation broth may be oriented such that the broth is a MAA-containing broth or a AA-containing broth. MAA, DAA, AA, ammonia and/or ammonium hydroxide may optionally be added to those broths to attain a broth pH preferably less than 6, optionally along with changing the ammonium balance to facilitate production of the above-mentioned substantially pure MAA. Also, it is possible that MAA, DAA and/or AA from other sources may be added as desired. In one particular form, it is especially advantageous to recycle MAA, DAA and water from the liquid bottoms resulting from the distillation step 24 and/or the liquid portion from the separator 34 into the fermentation broth. In referring to the MAA-containing broth, such broth generally means that the fermentation broth comprises MAA and possibly any number of other components such as DAA and/or AA, whether added and/or produced by bioconversion or otherwise.

The solid portion can be converted into AA by removing ammonia. This can be carried out as follows. The solid portion (consisting essentially of MAA) obtained from any of the above-described conversion processes can be dissolved in water to produce an aqueous MAA solution. This solution can then be distilled at a temperature and pressure sufficient to form an overhead that comprises water and ammonia, and a bottoms that comprises a major portion of AA, a minor portion of MAA and water. The bottoms can be cooled to cause it to separate into a liquid portion in contact with a solid portion that consists essentially of AA and is substantially free of MAA. The solid portion can be separated from the second liquid portion and recovered as substantially pure AA as determined by HPLC.

Figure 3:
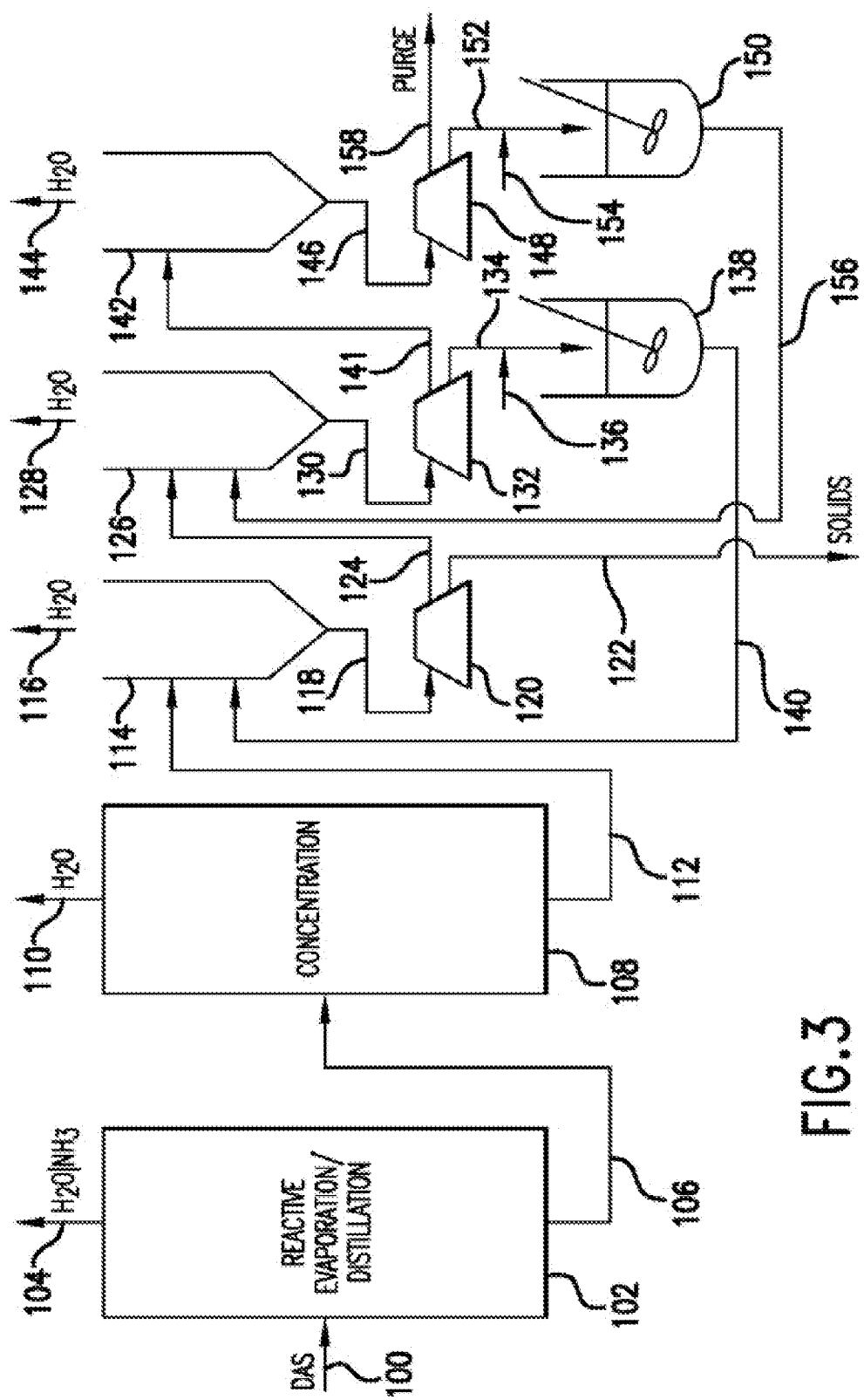
FIG. 3 is a flow diagram showing selected aspects of our process.

Turning to FIG. 3, we describe one of our particularly preferred processes. In FIG. 3, a stream 100 of DAA, which may be a stream of clarified fermentation broth which contains DAA (among other things), is subjected to reactive evaporation/distillation in distillation column 102. The distillation may occur over a range of temperatures such as about 110° C. to about 145° C., preferably about 135° C. The pressure in the distillation column 102 can be over a broad range about 1.5 to about 4 bar, preferably about 3.5 bar. Water and ammonia are separated in distillation column 102 and form an overhead 104. The liquid bottoms 106 comprises MAA, at least some DAA and at least about 20 wt. % water. Typically, bottoms 106 contains about 5 to about 20 wt. % MAA, about 80 wt. % to about 95 wt. % water and about 1 to about 3 wt. % DAA. The pH of the bottoms may be in a range of about 4.6 to about 5.6.

The bottoms 106 is streamed to a concentrator 108 which removes water via overhead stream 110. Concentrator 108 can operate over a range of temperatures such as about 90° C. to about 110° C., preferably about 100° C. and over a range of pressures such as at about 0.9 bar to about 1.2 bar, preferably about 1.103 bar.

Concentrator 108 produces a bottoms stream 112 which typically contains about 40 wt. % to about 70 wt. %, preferably about 55 wt. % MAA. Hence, the concentrator concentrates the amount of MAA typically by about 2 to about 11 times, preferably about 4 times to about 6 times.

Bottoms stream 112 flows to a first crystallizer 114 which operates at a temperature typically at about 50° C. to about 70° C., preferably about 60° C. A water overhead stream 116 is produced by the crystallizer. Bottoms 118 flows to a centrifuge 120 which produces a solid stream 122 which typically has a yield of MAA of about 95%. A remaining liquid flow 124 is sent to a second crystallizer 126 which removes additional water by way of overhead stream 128 and operates at a temperature typically at about 30° C. to about 50° C., preferably about 40° C. The bottoms stream 130 flows to a centrifuge 132. Centrifuge produces a solid stream 134 which is redissolved with a water stream 136 which introduces water in a temperature range typically of about 70° C. to about 90° C., preferably about 90° C. That stream flows to a first mixer 138 and produces a first recycle flow 140 back to the first crystallizer 114.

Remaining liquid from centrifuge 132 flows via stream 141 to third crystallizer 142 which produces an overhead stream 144 of water. Third crystallizer 132 typically operates at a temperature of about 10° C. to about 30° C., typically about 20° C. The remaining bottoms flow 146 streams to a third centrifuge 148 and solid material produced by third centrifuge 148 flows to a second mixer 150 by way of stream 152. That solid stream is dissolved by a second water stream 154 which introduces water typically at a temperature range of about 50° C. to about 70° C., preferably about 70° C. Second mixer 150 produces a recycle stream 156 which is recycled to second crystallizer 126. Remaining material flows outwardly of the system from third centrifuge 148 by way of purge stream 158 which typically represents about 5 wt. % of the total MAA contained in stream 112. It is understood that the desired crystallization temperatures in crystallizers 114, 126, and 142 can be attained by evaporation (as depicted), or by indirect contact with an external cooling medium, or a combination thereof.

EXAMPLES

The processes are illustrated by the following non-limiting representative examples. In all examples, a synthetic, aqueous DAA solution was used in place of an actual clarified DAA-containing fermentation broth.

The use of a synthetic DAA solution is believed to be a good model for the behavior of an actual broth in our processes because of the solubility of the typical fermentation by-products found in actual broth. Typically, the major by-products produced during fermentation are salts of monocarboxylic acids such as ammonium acetate, ammonium lactate and ammonium formate. If these impurities are present during the distillation step, one would not expect them to lose ammonia and form free acids in significant quantities until all of the DAA had been converted to MAA. This is because acetic acid, lactic acid and formic acid are stronger acids than the second acid group of AA (pKa=5.41). In other words, acetate, lactate, formate and even monohydrogen adipate are weaker bases than the dianion adipate. Furthermore, ammonium acetate, ammonium lactate and ammonium formate are significantly more soluble in water than MAA, and each is typically present in the broth at less than 10% of the DAA concentration. In addition, even if the acids (acetic, formic and lactic acids) were formed during the distillation step, they are miscible with water and will not crystallize from water. This means that the MAA reaches saturation and crystallizes from solution (i.e., forming the solid portion), leaving the acid impurities dissolved in the mother liquor (i.e., the liquid portion).

Example 1

This example demonstrates conversion of a portion of DAA into MAA via distillation and recovery of MAA solids from distillation bottoms liquid via cooling-induced crystallization.

A 1-L round bottom flask was charged with 800 g of a synthetic 4.5% diammonium adipate (DAA) solution. The flask was fitted with a five tray 1" Oldershaw section which was capped with a distillation head. The distillate was collected in an ice cooled receiver. The contents of the flask were heated with a heating mantel and stirred with a magnetic stirrer. Distillation was started and 719.7 g of distillate collected. Titration of the distillate revealed it was a 0.29% ammonia solution (i.e., an approximately 61% conversion of DAA to MAA). The hot residue (76 g) was discharged from the flask and placed in an Erlenmeyer flask and slowly cooled to room temperature while stirring over the weekend. The contents were then cooled to 15° C. for 60 minutes and then cooled to 10° C. for 60 minutes and finally 5° C. for 60 minutes while stirring. The solids were filtered and dried in a vacuum oven for 2 hours at 75° C. yielding 16.2 g. Analysis of the solids for ammonia content with an ammonia electrode indicated there was approximately a 1:1 molar ratio of ammonia and AA.

Example 2

This example demonstrates conversion of a portion of DAA into MAA via distillation.

The outer necks of a three neck 1-L round bottom flask were fitted with a thermometer and a stopper. The center neck was fitted with a five tray 1" Oldershaw section. The Oldershaw section was topped with a distillation head. An ice cooled 500 mL round bottom flask was used as the receiver for the distillation head. The 1-L round bottom flask was charged with distilled water, AA and concentrated ammonium hydroxide solution. The contents were stirred with a magnetic stirrer to dissolve all the solids. After the solids dissolved, the contents were heated with the heating mantle to distill 350 g of distillate. The distillate was collected in the ice cooled 500 mL round bottom flask. The pot temperature was recorded as the last drop of distillate was collected. The pot contents were allowed to cool to room temperature and the weight of the residue and weight of the distillate were recorded. The ammonia content of the distillate was then determined via titration. The results were recorded in Table 1.

TABLE 1

| | |
|---|---|
| Run # | 1 |
| Name of Acid | Adipic |
| Wt Acid Charged (g) | 14.62 |
| Moles Acid Charged | 0.1 |
| Wt 28% $NH_3$ Solution Charged (g) | 12.14 |
| Moles $NH_3$ Charged | 0.2 |
| Wt Water Charged (g) | 800.75 |
| Wt Distillate (g) | 350.46 |
| Wt Residue (g) | 466.65 |
| % Mass Accountability | 98.8 |
| Wt % $NH_3$ in distillate (titration) | 0.15 |
| Moles $NH_3$ in distillate | 0.031 |
| % Total $NH_3$ removed in Distillate | 15.5 |
| % First $NH_3$ removed in Distillate | 31 |
| $DiNH_4$/$MonoNH_4$ | 69/31 |
| Final Pot Temp (° C.) | 100 |
| Micromoles of $NH_3$/g distillate | 89 |
| Initial Wt % ammonium salt | 2.2 |
| $pKa_1$ | 4.43 |
| $pKa_2$ | 5.41 |
| $pKa_3$ | NA |

Example 3

This example demonstrates conversion of a portion of DAA into MAA in the presence of an ammonia releasing solvent via distillation and recovery of MAA solids from distillation bottoms liquid via cooling-induced crystallization.

A beaker was charged with 36.8 g of distilled water and 19.7 g of concentrated ammonium hydroxide. Then 23.5 g of adipic acid was slowly added. The mixture was stirred forming a clear solution which was then placed in a 500 mL round bottom flask which contained a stir bar. Triglyme (80 g) was then added to the flask. The flask was then fitted with a 5 tray 1" Oldershaw column section which was topped with a distillation head. The distillation head was fitted with an ice bath cooled receiver. The distillation flask was also fitted with an addition funnel which contained 150 g of distilled water. The contents were then stirred and heated with a heating mantel. When distillate began to come over the water in the addition funnel was added dropwise to the flask at the same rate as the distillate take-off. The distillation was stopped when all of the water in the addition funnel had been added. A total of 158 g of distillate had been collected. Titration of the distillate revealed a 1.6% ammonia content. This is equivalent to 46% of the charged ammonia. In other words the residue is a 91/9 mixture of monoammonium adipate/diammonium adipate. After cooling to room temperature, the residue was place in a 250 mL Erlenmeyer flask and slowly cooled to 5° C. while stirring. The slurry was filtered and the wet crystals were then dried in a vacuum oven for 2 hours yielding 5.5 g of solids. Analysis of the solids indicated essentially a one to one ratio of ammonium ion to adipate ion (i.e. monoammonium adipate).

Example 4

This example demonstrates the production of AA from MAA.

A 300 mL Parr autoclave was charged with 80 g of synthetic monoammonium adipate and 124 g of water. The autoclave was sealed and the contents stirred and heated to about 200° C. (autogenic pressure was about 203 psig). Once the contents reached temperature, water was then fed to the autoclave at a rate of about 2 g/min and vapor was removed from the autoclave at a rate of about 2 g/min with a back pressure regulator. Vapor exiting the autoclave was condensed and collected in a receiver. The autoclave was run under those conditions until a total of 1210 g of water had been fed and a total of 1185 g of distillate collected. The contents of the autoclave (209 g) were partially cooled and discharged from the reactor. The slurry was allowed to stand with stirring at room temperature over night in an Erlenmeyer flask. The slurry was then filtered and the solids rinsed with 25 g of water. The moist solids were dried in a vacuum oven at 75° C. for 1 hr yielding 59 g of adipic acid product. Analysis via an ammonium ion electrode revealed 0.015 mmole ammonium ion/g of solid. The melting point of the recovered solid was 151-154° C.

Example 5

This example demonstrates conversion of a portion of MAA into AA in the presence of an ammonia releasing solvent via distillation and recovery of AA solids from distillation bottoms liquid via cooling-induced crystallization.

A beaker was charged with 46.7 g of distilled water and 9.9 g of concentrated ammonium hydroxide. Then 23.5 g of adipic acid was slowly added. The mixture was stirred forming a clear solution which was then placed in a 500 mL round bottom flask which contained a stir bar. Triglyme (80 g) was then added to the flask. The flask was then fitted with a 5 tray 1" Oldershaw column section which was topped with a distillation head. The distillation head was fitted with an ice bath cooled receiver. The distillation flask was also fitted with an addition funnel which contained 1800 g of distilled water. The contents were then stirred and heated with a heating mantel. When distillate began to come over the water in the addition funnel was added dropwise to the flask at the same rate as the distillate take-off. The distillation was stopped when all of the water in the addition funnel had been added. A total of 1806.2 g of distillate had been collected. Titration of the distillate revealed a 0.11% ammonia content. This is equivalent to 72% of the charged ammonia. In other words the residue is a 72/28 mixture of adipic acid/monoammonium adipate. The residue was then placed in an Erlenmeyer flask and cooled to 0° C. while stirring and allowed to stand for 1 hr. The slurry was filtered yielding 18.8 g of a wet cake and 114.3 g of mother liquor. The solids were then dried under vacuum at 80° C. for 2 hrs yielding 13.5 g of solids. The solids were then dissolved in 114 g of hot water and then cooled to 5° C. and held stirring for 45 minutes. The slurry was filtered yielding 13.5 g of wet solids and 109.2 g of mother liquor. The solids were dried under vacuum at 80° C. for 2 hrs yielding 11.7 g of dried solids. Analysis of the solids revealed an ammonium ion content of 0.0117 mmol/g (i.e. essentially pure adipic acid).

Although our processes have been described in connection with specific steps and forms thereof, it will be appreciated that a wide variety of equivalents may be substituted for the specified elements and steps described herein without departing from the spirit and scope of this disclosure as described in the appended claims.

The invention claimed is:

1. A process for obtaining monoammonium adipate (MAA) from an aqueous clarified diammonium adipate (DAA)-containing fermentation broth comprising:
   (a) providing an aqueous clarified diammonium adipate (DAA)-containing fermentation broth;
   (b) distilling the broth to form an overhead that comprises water and ammonia, and a liquid bottoms that comprises MAA, at least some DAA, and at least 20 wt. % water;
   (c) cooling, evaporating or evaporative cooling the bottoms, and optionally adding an antisolvent to the bottoms, to attain a temperature and composition sufficient to cause the bottoms to separate into a DAA-containing liquid portion and a MAA-containing solid portion that is substantially free of DAA;
   (d) separating the solid portion from the liquid portion; and
   (e) recovering the solid portion.

2. The process of claim 1, wherein the solid portion is substantially free of adipamic acid, adipamide and adipimide.

3. The process of claim 1, wherein the antisolvent is selected from the group consisting of an alcohol, a ketone, and an ether.

4. A process for obtaining adipic acid (AA) from a clarified DAA-containing fermentation broth, comprising:
   (a) providing a clarified DAA-containing fermentation broth;
   (b) distilling the broth to form a first overhead that comprises water and ammonia, and a first liquid bottoms that comprises MAA, at least some DAA, and at least 20 wt. % water;
   (c) cooling, evaporating or evaporative cooling the first bottoms, and optionally adding an antisolvent to the first bottoms, to attain a temperature and composition sufficient to cause the first bottoms to separate into a DAA-containing first liquid portion and a MAA-containing first solid portion that is substantially free of DAA;
   (d) separating the first solid portion from the first liquid portion;
   (e) recovering the first solid portion;
   (f) dissolving the first solid portion in water to produce an aqueous MAA solution;
   (g) distilling the aqueous MAA solution at a temperature and pressure sufficient to form a second overhead that comprises water and ammonia, and a second bottoms that comprises a major portion of AA, a minor portion of MAA, and water;
   (h) cooling, evaporating or evaporative cooling the second bottoms to cause the second bottoms to separate into a second liquid portion and a second solid portion that consists essentially of AA and is substantially free of MAA;
   (i) separating the second solid portion from the second liquid portion; and
   (j) recovering the second solid portion.

5. The process of claim 4, wherein the first and second solid portions are substantially free of adipamic acid, adipamide and adipamide.

6. The process of claim 4, wherein the antisolvent is selected from the group consisting of an alcohol, a ketone, and an ether.

7. A process for obtaining MAA from an aqueous clarified MAA-containing fermentation broth comprising:
   (a) providing an aqueous clarified MAA-containing fermentation broth;
   (b) optionally adding an additional amount of at least one of MAA, DAA, AA, $NH_3$, and $NH_4^+$, to the broth depending on pH of the broth;
   (c) distilling the broth to form an overhead that comprises water and optionally ammonia and a liquid bottoms that comprises MAA, at least some DAA, and at least 20 wt. % water;
   (d) cooling, evaporating or evaporative cooling the bottoms, and optionally adding an antisolvent to the bottoms, to attain a temperature and composition sufficient to cause the bottoms to separate into a DAA-containing liquid portion and a MAA-containing solid portion that is substantially free of DAA;
   (e) separating the solid portion from the liquid portion; and
   (f) recovering the solid portion.

8. The process of claim 7, wherein the solid portion are substantially free of adipamic acid, adipamide and adipimide.

9. The process of claim 7, wherein the antisolvent is selected from the group consisting of an alcohol, a ketone, and an ether.

10. A process for obtaining AA from a clarified MAA-containing fermentation broth comprising:
   (a) providing a clarified MAA-containing fermentation broth;
   (b) optionally adding an additional amount of at least one of MAA, DAA, AA, $NH_3$, and $NH_4^+$, to the broth depending on pH of the broth;
   (c) distilling the broth to form an first overhead that comprises water and, optionally, ammonia and a first liquid bottoms that comprises MAA, at least some DAA, and at least 20 wt. % water;
   (d) cooling, evaporating or evaporative cooling the first bottoms, and optionally adding an antisolvent to the first bottoms, to attain a temperature and composition sufficient to cause the first bottoms to separate into a DAA-containing first liquid portion and a MAA-containing first solid portion that is substantially free of DAA;
   (e) separating the first solid portion from the first liquid portion;
   (f) dissolving the first solid portion in water to produce an aqueous MAA solution;
   (g) distilling the aqueous MAA solution at a temperature and pressure sufficient to form a second overhead that comprises water and ammonia, and a second bottoms that comprises a major portion of AA, a minor portion of MAA, and water;
   (h) cooling, evaporating or evaporative cooling the second bottoms to cause the second bottoms to separate into a second liquid portion and a second solid portion that consists essentially of AA and is substantially free of MAA;
   (i) separating the second solid portion from the second liquid portion; and
   (j) recovering the second solid portion.

11. The process of claim 10, wherein the first and second solid portions are substantially free of adipamic acid, adipamide, and adipimide.

12. The process of claim 10, wherein the antisolvent is selected from the group consisting of an alcohol, a ketone, and an ether.

13. A process for obtaining mono-X adipate (MXA) from a clarified DAA-containing fermentation broth comprising:
   (a) providing a clarified DAA-containing fermentation broth;
   (b) distilling the broth to form an overhead that comprises water and ammonia, and a liquid bottoms that comprises MXA, where X is at least one of $NH_4^+$, $Na^+$ and $K^+$, at least some di-Y adipate (DYA), where DYA includes DAA and at least one of disodium adipate (DNaA) and dipotassium adipate (DKA), and at least 20 wt. % water;
   (c) cooling, evaporating or evaporative cooling the bottoms, and optionally adding an antisolvent to the bottoms, to attain a temperature and composition sufficient to cause the bottoms to separate into a DYA-containing liquid portion and a MXA-containing solid portion that is substantially free of DYA;
   (d) separating the solid portion from the liquid portion; and
   (e) recovering the solid portion.

14. The process of claim 13, wherein the first and second solid portions are substantially free of adipamic acid, adipamide, and adipimide.

15. The process of claim 13, wherein the antisolvent is selected from the group consisting of an alcohol, a ketone, and an ether.

16. A process for obtaining MXA from a clarified MXA-containing broth, where X is at least one of $NR_4^+$, $Na^+$ and $K^+$ comprising:
   (a) providing a clarified MXA-containing broth;
   (b) optionally adding an additional amount of at least one of AA, $NH_3$, $NH_4^+$, $Na^+$, and $K^+$ to the broth to maintain the pH of the broth below 6;
   (c) distilling the broth to form an overhead that includes water and optionally ammonia, and a liquid bottoms that includes MXA, at least some DYA, where DYA includes at least one of DAA, DNaA and DKA, and at least 20 wt. % water;
   (d) cooling, evaporating or evaporative cooling the bottoms, and optionally adding an antisolvent to the bottoms, to attain a temperature and composition sufficient to cause the bottoms to separate into a DYA-containing liquid portion and a MXA-containing solid portion that is substantially free of DYA;
   (e) separating the solid portion from the liquid portion; and
   (f) recovering the solid portion.

17. The process of claim 16, wherein the first and second solid portions are substantially free of adipamic acid, adipamide, and adipimide.

18. The process of claim 16, wherein the antisolvent is selected from the group consisting of an alcohol, a ketone, and an ether.

19. A process for obtaining magnesium adipate from a clarified DAA-containing fermentation broth comprising:
   (a) providing a clarified DAA-containing fermentation broth;
   (b) distilling the broth to form an overhead that includes water and ammonia, and a liquid bottoms that includes MgA, at least some DAS and MgA and at least 20 wt. % water;
   (c) cooling, evaporating or evaporative cooling the bottoms, and optionally adding an antisolvent to the bottoms, to attain a temperature and composition sufficient to cause the bottoms to separate into a DAA and MgA -containing liquid portion and an MgA-containing solid portion that is substantially free of DAA;
   (d) separating the solid portion from the liquid portion; and
   (e) recovering the solid portion.

20. The process of claim 19, wherein the first and second solid portions are substantially free of adipamic acid, adipamide, and adipimide.

21. The process of claim 19, wherein the antisolvent is selected from the group consisting of an alcohol, a ketone, and an ether.

22. A process for obtaining MgA from a clarified MAA-containing fermentation broth comprising:
   (a) providing a clarified MAA-containing fermentation broth;
   (b) optionally adding an additional amount of at least one of AA, $NH_3$, $NH_4^+$ and $Mg^{+2}$ to the broth depending on pH of the broth;
   (c) distilling the broth to form an overhead that comprises water and optionally ammonia and a liquid bottoms that comprises MgA, at least some MAA, and at least 20 wt. % water;
   (d) cooling, evaporating or evaporative cooling the bottoms, and optionally adding an antisolvent to the bottoms, to attain a temperature and composition sufficient to cause the bottoms to separate into a MAA-containing liquid portion and a MgA-containing solid portion that is substantially free of MAA;
(e) separating the solid portion from the liquid portion; and
(f) recovering the solid portion.

23. The process of claim 22, wherein the first and second solid portions are substantially free of adipamic acid, adipamide, and adipimide.

24. The process of claim 22, wherein the antisolvent is selected from the group consisting of an alcohol, a ketone, and an ether.

* * * * *